(12) United States Patent
Baumfalk et al.

(10) Patent No.: US 9,095,498 B2
(45) Date of Patent: Aug. 4, 2015

(54) CONTAINER HAVING A COMPUTER PRODUCT

(75) Inventors: Reinhard Baumfalk, Goettingen (DE); Wolfgang Kahlert, Koerle (DE); Julia Lueders, Lahstedt (DE); Daniel Riechers, Hannover (DE)

(73) Assignee: SARTORIUS STEDIM BIOTECH GMBH (DE)

( * ) Notice: Subject to any disclaimer, the term of this patent is extended or adjusted under 35 U.S.C. 154(b) by 41 days.

(21) Appl. No.: 13/123,912

(22) PCT Filed: Oct. 6, 2009

(86) PCT No.: PCT/EP2009/007171
§ 371 (c)(1),
(2), (4) Date: Apr. 13, 2011

(87) PCT Pub. No.: WO2010/046029
PCT Pub. Date: Apr. 29, 2010

(65) Prior Publication Data
US 2011/0198255 A1    Aug. 18, 2011

(30) Foreign Application Priority Data

Oct. 22, 2008    (DE) .......................... 10 2008 052 693

(51) Int. Cl.
*A61J 1/10* (2006.01)
*B01L 3/00* (2006.01)
(Continued)

(52) U.S. Cl.
CPC .... *A61J 1/10* (2013.01); *B01L 3/52* (2013.01); *B01L 3/545* (2013.01);
(Continued)

(58) Field of Classification Search
CPC ............. B01L 3/08; B01L 3/54; B01L 3/545; B01L 3/5453; B01L 2300/022; B01L 2300/024; B01L 2300/025; B01L 2300/027; B01L 2300/041; B01L 3/505; A61J 1/10; A61J 2205/60
USPC .................................. 422/547, 549, 550, 555
See application file for complete search history.

(56) References Cited

U.S. PATENT DOCUMENTS

| | | | | |
|---|---|---|---|---|
| 3,909,773 | A | * | 9/1975 | Saltzer ......................... 367/134 |
| 4,563,758 | A | * | 1/1986 | Paternostro ................... 367/132 |
| 2008/0279724 | A1 | * | 11/2008 | Dicarlo ........................... 422/58 |

FOREIGN PATENT DOCUMENTS

| | | |
|---|---|---|
| WO | 00/42969 | 7/2000 |
| WO | 2004/008387 | 1/2004 |

(Continued)

OTHER PUBLICATIONS

International Preliminary Report on Patentability.

*Primary Examiner* — Jill Warden
*Assistant Examiner* — Dwayne K Handy
(74) *Attorney, Agent, or Firm* — Gerald E. Hespos; Michael J. Porco; Matthew T. Hespos

(57) ABSTRACT

A storage and/or reaction container system for fluids, includes a container and an electronic documentation device connected to the container. The documentation device further includes a timing device for capturing a point in time, at least one sensor, at least one input device for capturing inputs, and a storage device to store for readout at least one measured value captured by the at least one sensor device and/or an input captured by the at least one input device. The at least one measured value and/or the at least one input is associated by the timing device with the point in time of the capture.

23 Claims, 3 Drawing Sheets

(51) Int. Cl.
  *G01N 35/00* (2006.01)
  *A61J 1/14* (2006.01)
  *G01N 35/10* (2006.01)

(52) U.S. Cl.
  CPC ............ *G01N 35/00732* (2013.01); *A61J 1/14* (2013.01); *A61J 2200/72* (2013.01); *A61J 2205/20* (2013.01); *A61J 2205/60* (2013.01); *A61J 2205/70* (2013.01); *B01L 2200/143* (2013.01); *B01L 2200/148* (2013.01); *B01L 2300/022* (2013.01); *B01L 2300/023* (2013.01); *B01L 2300/024* (2013.01); *B01L 2300/027* (2013.01); *G01N 35/1002* (2013.01); *G01N 2035/00633* (2013.01); *G01N 2035/00673* (2013.01); *G01N 2035/00851* (2013.01); *Y10T 29/49826* (2015.01)

(56) References Cited

FOREIGN PATENT DOCUMENTS

| | | |
|---|---|---|
| WO | 2006/040106 | 4/2006 |
| WO | 2006/086489 | 8/2006 |

\* cited by examiner

CONTAINER HAVING A COMPUTER PRODUCT

BACKGROUND OF THE INVENTION

1. Field of the Invention

The present invention relates to a container system, the use of a container system and a method for producing a container system.

2. Description of the Related Art

In the case of non-clinical, experimental testing of substances or preparations, the results of which should allow the authorities to evaluate possible risks to humans and the environment, the Chemikaliengesetz [Chemicals Act] makes the observance of "good laboratory practice" (GLP) principles mandatory. The ChemVwV-GLP [chemical administrative regulation—good laboratory practice] substantiates the field of application for chemicals, pesticides, medicaments, explosives, in the transport of dangerous goods, and for food and feed additives.

In order to ensure reliable and complete documentation of a manual process step in a test series, more particularly such that it conforms to GLP, the user (member of staff) conducting said tests is advised to carry out the documentation of the relevant process parameters immediately after carrying out the action. These days, this is still primarily carried out by means of paper records, because this can be integrated into the progression of the test series in a quick and simple fashion. However, the long-term documentation of the process parameters is generally in digital form, and so the documented data must subsequently be digitized. This step of data migration is time consuming and is subject to additional monitoring as to whether the data was transferred correctly. Alternatively, the recorded process parameters and performance acknowledgements could be entered directly into an electronic recording system, but this is only reluctantly accepted due to the additional paths for the users in the case of fixedly installed recording systems and it is difficult to bind this into the procedure.

WO 2006/040106 A1 discloses a self-contained disposable analysis device for qualitative and quantitative examination of samples. The disposable analysis device comprises a sensor, for measuring a chemical or physical property of a substance, and a data-recording device with a data storage medium, wherein the sensor and the data-recording device are integral components of a packaging made of a sheet-like, printable and foldable material, which surrounds and protects all components.

WO 2006/086489 A1 discloses a monitoring system for a bioreactor with a monitoring unit designed to obtain information relating to the conditions or states in the bioreactor and to control the processes in the bioreactor.

WO 00/42969 A1 discloses a device for monitoring the quality of a liquid stored in a container and for identifying said liquid. To this end, an integrated circuit is arranged on the container; said integrated circuit is connected to sensors and it stores the measured values, recorded by the sensors, by means of a processor unit or transmits said measured values to an external computer.

It is an object of the present invention to simplify the recording and documentation of relevant process parameters over the full duration of a test series, and to increase the reliability of the documentation. This object is achieved by the subject matter of the independent claims. Preferred embodiments are the subject matter of the dependent claims.

SUMMARY OF THE INVENTION

One aspect of the present invention relates to a container system, more particularly a storage and/or reaction container system for liquids, comprising: a container and an electronic documentation device connected to the container, wherein the documentation device furthermore comprises: a timer for recording a time, at least one sensor device, at least one entry device designed in order to record entries, and a storage apparatus designed to store at least one measured value recorded by the at least one sensor device and/or an entry recorded by the at least one entry device such that the stored item(s) can be read. The timer is used to associate the at least one measured value and/or the at least one entry with a time corresponding to when it/they was/were recorded.

Advantageously, the documentation device is arranged on the container, more particularly affixed to the latter, such that the measured values and/or entries (process parameters in general) documented by the documentation device can easily be associated with the associated container. It is further advantageous that the process parameters can be documented directly after a process step on the treated sample or the container thereof by the user carrying out the process. This process step can comprise: a visual inspection, filling, emptying, initiating a chemical, biological and/or physical process, etc. It is further advantageous that, in addition to a process parameter, the recording time is likewise stored in the documentation device, and so, while a test series is carried out or after completion thereof, all recorded process parameters are available as a time series and can optionally be evaluated as a time series, as a result of which retrospective processing of recorded process parameters for evaluation purposes is simplified.

A container within the scope of the invention is distinguished by the fact that the container is designed to be sufficiently impermeable in respect of the contents of the container to be contained, such that the contents of the container (or parts thereof) cannot, contrary to purpose, be displaced beyond the geometric confines of the container. The term "sufficiently impermeable" can, within the scope of the invention, mean that, in particular, the container is impermeable to particles, preferably to particles with a particle diameter of more than approximately 1 mm, more preferably to particles with a particle diameter of more than approximately 100 $\mu$m, 50 $\mu$m, 10 $\mu$m, particularly preferably to particles with a particle diameter of more than approximately 5 $\mu$m, 2 $\mu$m, 1 $\mu$m. Within the scope of the invention, it is further preferable that the term "sufficient impermeable" can mean that the container is substantially watertight, moisture-tight, water-vapor-tight, airtight, gastight, shielding-gas-tight, inert-gas-tight and/or fluid-tight (more particularly fluid-tight to shielding gases such as helium, argon, nitrogen, carbon dioxide, etc.), such that the interior of the container is substantially entirely closed off from the environment in a watertight, moisture-tight, water-vapor-tight, airtight, gastight and/or fluid-tight fashion.

The term "substantially impermeable" can describe a minor deviation from complete impermeability, more particularly it encompasses a small leakiness or a leakage rate of less than approximately 30%, less than approximately 20%, less than approximately 10%, less than approximately 5%, less than approximately 2%, preferably less than approximately 1% of the contents of the container per year. The term "substantially" comprises the term "completely" or "identical", i.e. without leakiness or with a leakage rate of approximately 0%.

The timer provides, in particular, a date, a time, a clock and/or a counter reading, etc., and so the value provided by the timer and/or the measured value recorded by the sensor device and/or the entry recorded by the entry device can be associated unambiguously with a time.

The storage apparatus is designed to store data—such as the recording time, a measured value and/or an entry—such that the stored item(s) can be read. Here, a time of the recording or a recording time can be, or is, unambiguously associated with the at least one measured value and/or the at least one entry. More particularly, the time of the recording is stored together with a measured value and/or an entry such that the stored item(s) can be read. More particularly, the storage apparatus can also store an unambiguous identification number of the container system, and/or a batch number and/or sample number of the contents of the container. Here, the data can be read by the documentation device and/or by an external device, wherein the read-out can take place before, during and/or after the operational use of the container system. More particularly, in the storage apparatus, the data can be stored permanently or in a non-volatile fashion and/or in an unalterable fashion. In this context, "permanent" or "non-volatile" means that the stored data remains available for read-out without there being an external energy supply in the storage apparatus, i.e. the stored data is not merely stored in a volatile fashion. In conjunction with data stored in the storage apparatus, "unalterable" means that the data cannot be changed and/or deleted after the storage procedure. More particularly, the storage apparatus can comprise an EPROM, an EEPROM or a flash-memory. The container system and/or the contents thereof advantageously can be unambiguously identified by the storage apparatus, wherein a complete chronological log of the states of the container system or the contents is provided.

The container preferably consists of a flexible plastic. In this context, flexible means that the plastic is elastic and preferably has good elastic recovery. More particularly, the container can at least in part or in sections be made of polyethylene, polyvinyl chloride or polycarbonate. Containers made from one of these plastics advantageously are simple to produce and are chemically inert with respect to a multiplicity of substances.

The container is preferably a disposable container, particularly preferably a sterilizable disposable container. It is further preferable that the container is designed to be sterilizable by autoclaving, i.e. the container is designed to be substantially inherently stable at temperatures up to approximately 100° C., preferably up to approximately 120° C., more preferably up to approximately 150° C. The container is particularly preferably designed to be sterilizable by sterilization means, in particular by ethylene oxide and/or ethyl alcohol, i.e. the container material does not dissolve in ethyl alcohol in particular. The container is further preferably designed to be sterilizable by means of gamma radiation.

The term "substantially" in respect of the inherent stability may describe a minor deviation from an intended shape after temperature application, more particularly it may describe a deviation in line with the production accuracy and/or in line with the necessary accuracy, and so an effect is retained as is present in the case of the intended shape. In particular, the term "substantially" can therefore encompass a deviation of less than approximately 30%, less than approximately 20%, less than approximately 10%, less than approximately 5%, less than approximately 2%, preferably less than approximately 1% from an intended shape. The term "substantially" comprises the term "identical", i.e. without deviation from an intended shape.

The at least one entry device is preferably designed in order to record a manual actuation. A manual actuation more particularly comprises pressureless touching, the application of a force or the spatial displacement of the entry device. More particularly, the at least one entry device can comprise a photoresistor or an electrical conductivity sensor for detecting a touching of the entry device, in particular by a finger. It is further preferable for the at least one entry device to comprise at least one position sensor, more particularly a mercury switch and/or an inertia sensor, designed to detect a spatial rotation and/or translation of the entry device.

The at least one entry device preferably comprises at least one push-button and/or at least one switch, which is/are preferably part of the documentation device. In particular, the at least one entry device comprises a keyboard designed to record numeric or alphanumeric entries by users. Advantageously, manual entries of the binary type, that is to say acknowledgements—of a visual inspection which is due, for example—, can be made particularly easily by the provision of a push-button and/or a switch on the entry device.

The at least one entry device preferably comprises a receiving device designed in order to record a signal from an external device. The receiving device is preferably designed to record entries by users via an external device. In particular, numeric or alphanumeric user entries can be recorded by means of an external keyboard and/or an external computer, transmitted to the receiving device, and stored by the documentation device. The transmission can for example take place via a Bluetooth, LAN, WLAN, Firewire, USB, and/or radio connection. Comprehensive entries (e.g. observations or descriptions of events) by the user advantageously can be recorded in the documentation device in a simple fashion via the receiving device, more particularly via an external keyboard.

The at least one receiving device preferably comprises an electromagnetic coupling element and/or a capacitive coupling element and/or an inductive coupling element and/or a direct coupling element. In particular, the receiving device can comprise an antenna (e.g. an RFID antenna), a coil, an infrared receiver, an electrical connector, a fiber-optic connector, etc.

The container preferably has a sealing apparatus. The sealing apparatus is preferably designed to separate the interior of the container from the exterior. The separation is impermeable, more particularly fluid-tight and/or sterile.

The sealing apparatus preferably comprises a film and/or at least one metal conductor and/or an electrically conductive polymer. In particular, the sealing apparatus comprises a sterile membrane. More preferably, the sealing apparatus comprises a film made of electrically non-conductive material, in which thin threads or wires of an electrically conductive material are embedded.

The at least one sensor device preferably detects the sealing state of the sealing apparatus, wherein the associated time of the recording preferably corresponds to a break of the sealing apparatus. The at least one sensor device particularly preferably detects changes in the electrical conductivity of an electrically conductive part of the sealing apparatus, more particularly of an electrically conductive film and/or electrically conductive wires or threads embedded in the sealing apparatus or in a film.

The sealing apparatus further preferably comprises a valve, more particularly a rotary valve, and/or a fastener, more particularly a screw-top fastener or a tear-off fastener. An electrically conductive region is preferably formed on the valve or the fastener, and so the state of the valve or the faster (open/closed) can be detected by virtue of the fact that the electrically conductive region of the valve or fastener closes or does not close an electrical circuit.

A break in the seal advantageously can be documented by the sensor device, which detects the sealing state of the sealing apparatus, for example the opening of a starting material required in a test series, banked blood or the like. As a result, it is always possible to trace from what time the contents of the container were no longer sterile, such that the shelf-life of the contents in open storage conditions starts at this time. This advantageously allows a quality control of the utilized contents at all times; more particularly, it is also possible to determine, after a test series was carried out, whether use was made at any time in the test series of expired starting materials.

To this end, preferably the production date, the sterilization date, the expiry date of the bag, the expiry date of the contents under sterile conditions and/or the expiry date of the contents under non-sterile conditions can be or are stored in the storage apparatus, and can be read out therefrom.

The at least one sensor device preferably comprises a temperature sensor and/or a photosensor and/or an electrical resistance sensor and/or an electrical conductivity sensor and/or a pH sensor and/or a sensor for determining the concentration of dissolved gases and/or the concentration of substances present in the container interior (for example oxygen, carbon dioxide and/or chlorophyll) and/or a sensor for determining a particle and/or cell density. More particularly, the photosensor is designed to carry out a photometric measurement, for example determining a dimming or a color change. The at least one sensor device particularly preferably comprises a non-invasive sensor, i.e. a sensor allowing the measurement of a parameter without losing the integrity of the container or without contacting the interior of the container. More particularly, the non-invasive sensors are designed as disposable sensors.

The documentation device preferably comprises at least one indicator device for indicating a state of the documentation device and/or contents stored in the storage apparatus to a user.

The at least one indicator device preferably comprises at least one visual indicator and/or at least one acoustic indicator and/or at least one haptic indicator. More particularly, the indicator device comprises a light-emitting diode (more particularly multicolored LEDs, e.g. a red LED as a warning signal) and/or an alphanumeric indicator (display, more particularly LCD or film display). The indicator device further preferably comprises a piezoelectric sound source and/or a loudspeaker. The indicator device particularly preferably comprises a vibrating alarm. The indicator device advantageously can signal that a process parameter, for example the temperature or damage to the seal, has reached or exceeded a threshold that is or can be predetermined. In particular, in this case the indicator device can be used to request an acknowledgement from a user via the entry device. In particular, this allows a distinction to be made as to whether damage to the seal of the container was deliberate or unintentional.

The documentation device preferably comprises at least one transmitting device designed in order to transmit a state of the documentation device and/or contents stored in the storage apparatus to an external device. More particularly, the external device can be a computer designed to receive, store and/or process further the data transmitted by the transmitting device. The transmission from the transmitting device to the external device can take place via a Bluetooth, LAN, WLAN, Firewire, USB, and/or radio connection, for example. The at least one transmitting device is particularly preferably identical to at least one receiving device of the documentation device.

The at least one transmitting device preferably comprises an electromagnetic coupling element and/or a capacitive coupling element and/or an inductive coupling element and/or a direct coupling element. In particular, the transmitting device can comprise an antenna, a coil, an infrared receiver, an electrical connector, a fiber-optic connector, etc.

The documentation device preferably comprises a current source. The current source comprises, in particular, a current-storage device, for example a battery, a rechargeable battery and/or a capacitor. The current source further preferably comprises a current-generating apparatus, for example a solar cell, a fuel cell and/or an inductive component (e.g. a coil), which generates an electrical current from a time-varying magnetic field permeating the component (e.g. a high-frequency antenna). In particular, the current source is designed to allow continuous operation of the documentation device including the sensors. More preferably, the documentation device is operated in intervals, more particularly in periods of less than 60 s, less than 30 s, less than 10 s or less than 5 s.

The documentation device preferably further comprises a signal-processing device, more particularly a microcontroller and/or a CPU.

The documentation device preferably is flexible. In this context, flexible means that the documentation device is elastic and preferably has good elastic recovery. More particularly, the documentation device comprises a flexible printed circuit board. The documentation device, more particularly excluding the sensors, is preferably thinner than 5 mm, more preferably thinner than 3 mm, more particularly thinner than 2 mm. It is particularly preferable for the longest edge length of the documentation device, more particularly excluding the sensors, to be preferably less than 10 cm, more preferably less than 5 cm, more particularly less than 2 cm.

It is further preferable for the documentation device to be designed to be sterilizable together with the container. More particularly, the documentation device can be sterilized by means of steam, ethylene oxide, ethanol, and/or gamma irradiation. That is to say the documentation device is designed to remain substantially inherently stable and operational during autoclaving at temperatures of up to approximately 100° C., preferably up to approximately 120° C., more preferably up to approximately 150° C. It is particularly preferable for the documentation device to be designed to be insoluble in ethyl alcohol; the documentation device is fluid-tight in particular. The documentation device is further preferably designed to be functional after gamma-ray sterilization. More particularly, the documentation device is shielded from gamma radiation.

The documentation device is preferably permanently connected to the container by welding and/or adhesive bonding and/or embedding. That is to say the documentation device is preferably attached to or in the container by welding on, welding in, partial or complete embedding and/or adhesive bonding, more particularly said documentation device is attached such that the container system becomes unusable by removing the documentation device.

A further aspect of the present invention relates to the use of a container system according to the invention as a storage container and/or reaction container and/or disposable container in an application requiring documentation.

The documentation requirement can, in particular, relate to all original laboratory records which have to be recorded in their entirety, be readable and be suitable and necessary for reconstructing an examination. In particular, this includes a clear association between the collected data items and the person collecting them; complete traceability of changes (date, time, person undertaking the change, reasons for change); maintaining the original data after a change. All these requirements are advantageously satisfied by the container system according to the invention.

A further aspect of the present invention relates to a method for producing a container system, comprising the steps of: providing a container, providing an electronic documentation device with a timer for recording a time, at least one sensor device and at least one entry device designed in order to record entries, and a storage apparatus designed to store at least one measured value recorded by the at least one sensor device and/or an entry recorded by the at least one entry device such that the stored item(s) can be read. The timer is used to associate the at least one measured value and/or the at least one entry with a time corresponding to when it/they was/were recorded. The method further includes arranging the documentation device on the container.

Arranging the documentation device can preferably comprise attaching or connecting, more particularly permanent attaching or connecting.

The method preferably furthermore comprises the step of: attaching, at least in sections, the at least one sensor device onto the container.

The method preferably furthermore comprises the step of: synchronizing the timer. The synchronization can be carried out by synchronizing the timer with an external timer, by writing the current time of the external timer to the timer of the documentation device, for example by means of the entry device. Alternatively, the current time of the external timer can be stored in the storage apparatus together with the current time of the timer, in order to document the time difference. The time difference is preferably documented periodically in order to document a time response of the timer. The external time source can, in particular, be a time signal transmitted by radio waves, e.g. DCF77.

The method preferably furthermore comprises the step of: closing the container by means of a sealing apparatus. In particular, closing can be brought about in a sterile and/or fluid-tight fashion.

The method preferably furthermore comprises the step of: sterilizing the container system. The sterilization is preferably effected by autoclaving, by means of sterilization means (e.g. ethylene oxide and/or ethyl alcohol) or by gamma-ray irradiation.

The method preferably furthermore comprises the step of: storing the production date and/or the batch number and/or the expiry date in the storage apparatus.

The preceding description of the aspects of the invention is not restricted to the respective aspects. Rather, the explanations relating to the respective aspects apply analogously to the further aspects of the invention. In particular, the explanations in respect of the container system also apply to the use and vice versa, and also to the method or preferred embodiments and/or embodiment variants thereof.

In the following text, preferred embodiments of the present invention are described in an exemplary fashion with reference to the attached figures. Individual elements of the described embodiments are not restricted to the respective embodiment. Elements of the exemplary embodiments can rather be combined with one another in any combination, and new embodiments can be created thereby.

DETAILED DESCRIPTION OF THE PREFERRED EMBODIMENT

Figure 1:
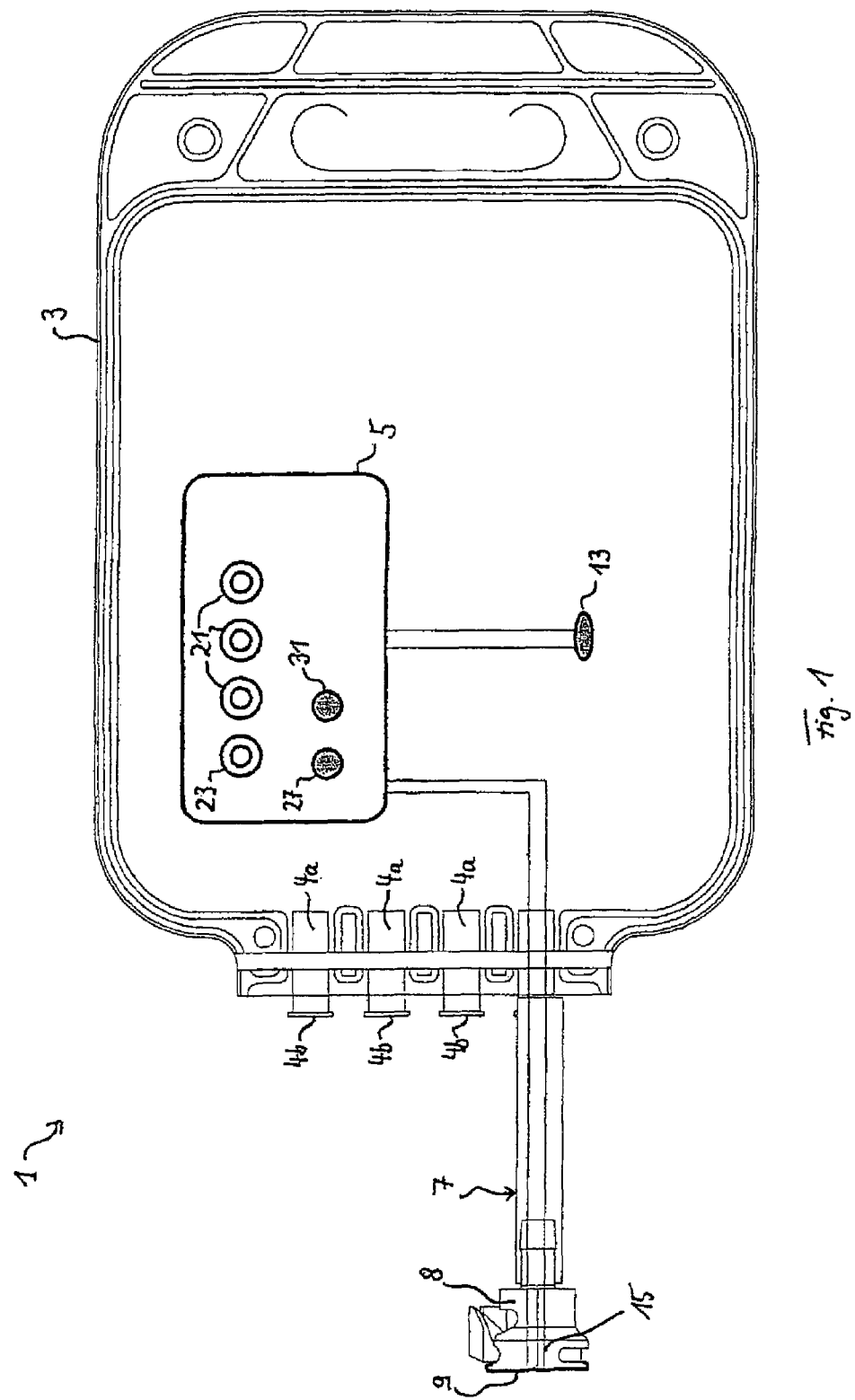
FIG. 1 shows a plan view of a container system.

FIG. 1 shows a plan view of a container system 1. The illustrated preferred embodiment comprises a container 3, which is designed as a sterilizable disposable bag made of flexible plastic. This preferred container is designed to be used in the field(s) of medicine and/or biotechnology and therefore has connections 4a with sterile tear-off flaps 4b for filling and/or emptying the container 3.

Arranged on one of the connections 4a there is a tube connection 7, with a tube connector 8 forming the closure at the end thereof. The tube connector 8 has a sealing apparatus 9 with a fluid-tight metal film, which separates the interior of the tube connector 8, tube connection 7 and container 3 from the exterior in a sterile fashion. As an alternative to the metal film, or in addition thereto, the sealing apparatus 9 can also comprise a film made of an electrically conductive polymer.

Figure 2:
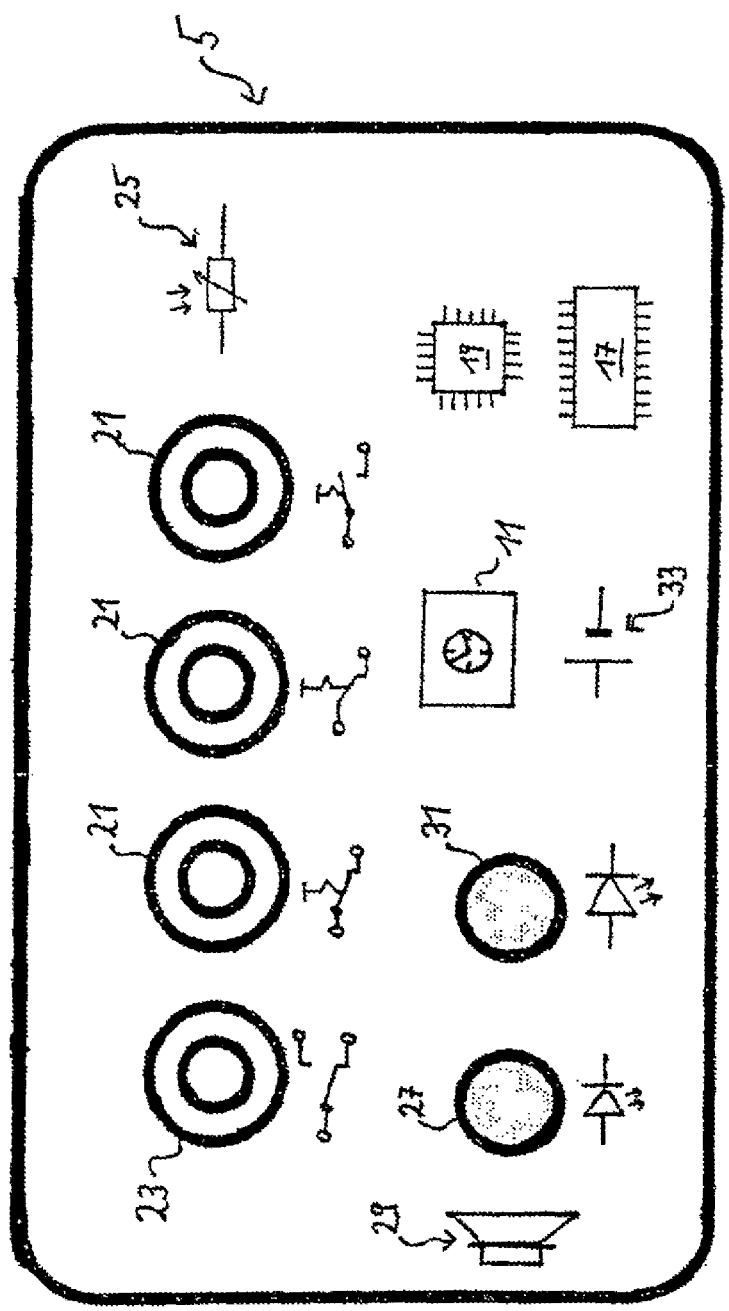
FIG. 2 shows a detailed view of a documentation device.

The container 3 is permanently connected to an electronic documentation device 5 (shown in detail in FIG. 2). That is to say the documentation device 5 has preferably been attached to the container 3 by welding on, welding in and/or adhesive bonding such that the container system 1 becomes visibly unusable by detaching the documentation device 5. In particular, the container 3 is destroyed.

In this embodiment, the documentation device 5 comprises two sensor devices, and specifically a temperature sensor 13 and an electrical conductivity sensor 15. The temperature sensor 13 is arranged on the container 3 such that said temperature sensor 13 substantially records the temperature of the contents of the container 3. The electrical conductivity sensor 15 is arranged on the tube connector or the sealing apparatus 9, such that said electrical conductivity sensor 15 substantially records the electrical conductivity of the metal film of the sealing apparatus 9. A change in the electrical conductivity of the metal film, more particularly a reduction in the electrical conductivity, is recorded by the electrical conductivity sensor 15, with this event being documented by the documentation device 5 as a possible break of the seal.

As an alternative to the temperature sensor 13 and the electrical conductivity sensor 15, or in addition thereto, the documentation device 5 can likewise comprise a photosensor and/or an electrical resistance sensor and/or a pH sensor and/or a sensor for determining the concentration of dissolved gases and/or the concentration of substances present in the container interior (for example oxygen, carbon dioxide and/or chlorophyll) and/or a sensor for determining a particle and/or cell density. More particularly, the photosensor can be designed to carry out a photometric measurement. To this end, the photosensor can be arranged at a defined distance from a light source in order to determine, by means of the occurring photometric extinction, for example a dimming or a color change as a result of a chemical reaction. The at least one sensor device preferably comprises a non-invasive sensor, i.e. a sensor that allows the measurement of a parameter without losing the integrity of the container or without contacting the interior of the container or without penetrating even slightly therein. A non-invasive sensor is or can be preferably arranged at or on the exterior wall of the container 3, or in the vicinity thereof. In particular, the non-invasive sensors are designed as disposable sensors.

FIG. 2 shows a detailed view of a documentation device 5. The illustrated documentation device 5 comprises three push-buttons 21, a switch 23 and a receiving device 25 as preferred entry devices 21, 23, 25. Moreover, the documentation device 5 comprises a timer 11 and a storage apparatus 17 which is designed to store the measured values, recorded by the temperature sensor 13 and by the electrical conductivity sensor 15, and the entries, recorded by the entry devices 21, 23, 25, together with the recording time provided by the timer 11 such that the stored item(s) can be read.

The push-buttons 21 and the switch 23 are designed in order to record a manual actuation by a user. A manual actuation more particularly comprises the substantially pressureless touching of the push-buttons 21. To this end, the push-buttons 21 can for example be embodied as photoresistors 21, which can detect covering—i.e. pressureless touching—by a finger. Furthermore, the push-buttons 21 can be designed as electrical contact sensors 21, which can detect an electrical bridging by the skin of a finger. By contrast, the switch 23 can for example be embodied as a sliding switch 23, which changes its position as a result of a user applying a force. The documentation device 5 can, for example, record acknowledgements in a simple fashion by means of the push-buttons 21.

The receiving device 25 is designed in order to record a signal from an external device. In this embodiment, the receiving device comprises an infrared sensor in order to communicate with an external device by means of an infrared connection. In particular, numeric and/or alphanumeric user entries can be recorded by means of an external keyboard and/or an external computer, transmitted to the receiving device and stored by the documentation device. Alternatively, or in addition thereto, the receiving device can comprise an antenna, a coil, an electrical connector, a fiber-optic connector, etc.

The illustrated documentation device 5 comprises a visual indicator 27, an acoustic indicator 29 as preferred indicator device, and also a transmitting device 31. The visual indicator comprises a light-emitting diode 27. Alternatively, or in addition thereto, the visual indicator can likewise comprise an alphanumeric indicator, such as a 7-segment indicator or an LCD display for example. The acoustic indicator 29 preferably comprises a piezoelectric sound source 29.

The transmitting device 31 is designed in order to transmit a state of the documentation device 5 and/or contents stored in the storage apparatus 17 to an external device, for example a computer. The transmitting device 31 can comprise an infrared diode as a preferred embodiment, in order to communicate with the external device by means of an infrared connection. Alternatively, or in addition thereto, the transmitting device 31 can also comprise an antenna, a coil, an electrical connector, a fiber-optic connector, etc.

In particular, a transmitting device 31 can be identical to a receiving device 25. More particularly, an antenna or an electrical connector can be both a transmitting device 31 and a receiving device 25 within the scope of the invention.

The storage apparatus 17 is designed to store data such as the recording time, a measured value and/or an entry, such that the stored item(s) can be read. More particularly, the storage apparatus 17 can comprise an EPROM, an EEPROM or a flash-memory, wherein the (read/write) access to the storage apparatus 17 can be brought about by means of a signal-processing device 19, for example a microcontroller.

The documentation device 5 comprises a current source 33 for supplying said documentation device 5 with energy. The current source 33 in particular comprises a battery 33 or a rechargeable battery 33, which is designed to supply the documentation device 5 with current, at least until the expiry date of the container system 1.

Alternatively, or in addition thereto, the current source can comprise a current-generating apparatus that generates current continuously or at discrete times, which current can, in particular, be stored in a rechargeable battery and/or capacitor. By way of example, a current-generating apparatus can be a solar cell and/or an inductive component (e.g. a coil), wherein light, impinging on a solar cell, and an external alternating magnetic field, applied to the inductive component, is converted into electrical current.

An exemplary maintenance history of a preferred embodiment of the container system 1 will be described in the following text, wherein features that are identical to the features described with reference to FIGS. 1 and 2 are provided with the reference signs used in said figures. The events described below and at least partially stored by the documentation device 5 are summarized in the following table 1 as an exemplary product or batch log and/or "batch record".

A container 3 is permanently connected to the documentation device 5 during the production process. Here the container 3 has a tube connection 7 with a tube connector 8, wherein the tube connector 8 has a sealing apparatus 9. A temperature sensor 13 is connected to the container 3 and an electrical conductivity sensor 15 is connected to the sealing apparatus 9.

The documentation apparatus 5 has an RFID antenna as preferred transmitting and receiving device, by means of which the serial number, the production date and the expiry date of the container system 1 are moved, from an external apparatus, to a storage apparatus 17 and stored therein. A timer is synchronized using an external time source. It goes without saying that other transmitting and receiving devices can also be used instead of the RFID antenna, for example transmitting and receiving devices that are suitable for setting up an infrared, Bluetooth, Ethernet, Firewire and/or USB connection to an external device.

Figure 3:
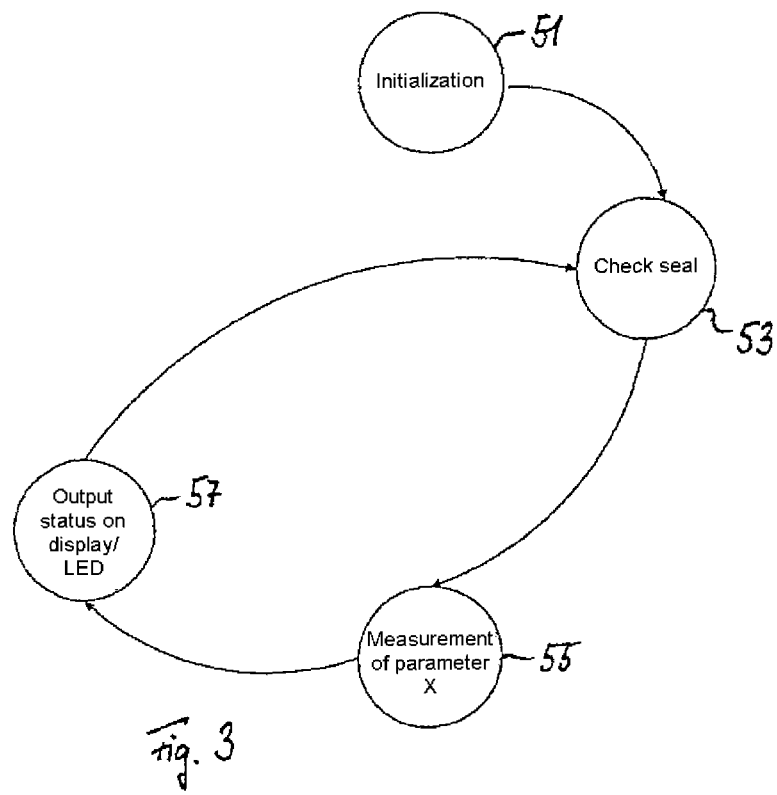
FIG. 3 shows a flowchart for recording the state.

The container system 1 is packaged and sterilized. As illustrated in FIG. 3, the producer documents the product data, more particularly the date of production and the expiry date or use-by date, as an initial event or first event or as initialization step 51 in the product log(see table 1, row 1), wherein the container system preferably is initially provided with a blocking flag (in table 1: status "B" for "blocked"). After production, the container system is examined for quality control and stored after successful examination. The result of the quality control is transmitted in a release log to the documentation device 5, in particular as a PDF document, via the RFID antenna, and is at least partially stored in said device (see table 1, row 2). A container system released by the producer obtains the status "OK" and can subsequently be delivered to a user.

After initialization, the documentation device 5 continuously or periodically performs a sealing-state-recording step 53 and/or a measured-value-recording step 55, wherein, in a status-indication step 57, the status of the container system 1 is preferably indicated by means of an indicator device. Here, in particular, the green glow of an LED 27 can indicate that the status of the container system is set to "OK".

The user can use a wireless connection by means of the RFID antenna of the documentation device 5 to make a stock check or store status information (received on . . . /storage location/etc.) in the storage apparatus (see table 1, row 3).

In order to be used, the container system 1 is unpacked and examined in respect of usability. A successful examination can be logged in the documentation device 5. A push-button 21 allows the storing of a use-release including the release time by a user after a performed, and successful, visual inspection of the container system 1 (see table 1, row 4). The successful storing of this event is signaled by green lighting-up of an LED 27. A malfunction brings about red lighting-up of the LED 27 and/or acoustic feedback via a piezo-loudspeaker 29.

Figure 4:
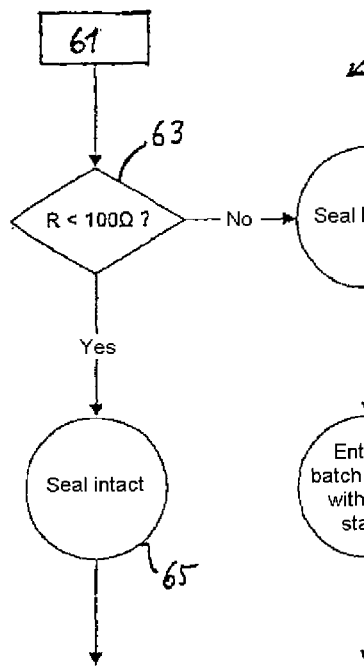
FIG. 4 shows a flowchart for recording a break of the seal.

The container system 1 has to be prepared manually for a process step, e.g. by filling the container 3 with a sample. The filling requires unsealing of the sealing apparatus 9. The unsealing is detected or recorded during the sealing-state-recording step 53, illustrated in FIG. 4, wherein this event is stored together with the recording time, i.e. the time of the unsealing, in the storage apparatus 17 (see table 1, row 5).

The sealing-state-recording step 53 preferably comprises the continuous or periodic measurement of the electrical conductivity and/or the electrical resistance R of the sealing apparatus 9 or an electrical conductor thereof by means of a sensor device 15, preferably in a resistance-recording step 61. If the electrical resistance undershoots a specific (predetermined or predeterminable) threshold, for example 100 ohm, in a comparison step 63, the sensor device 15 outputs the state message "seal intact" in an output step 65. If the electrical resistance exceeds the specific (predetermined or predeterminable) threshold, the sensor device 15 outputs the state message "seal broken" in an output step 67. The documentation device logs the break of the seal together with the recording time in step 69.

An acknowledgement by the user is preferably required after unsealing, in order to confirm a usage-required unsealing and to differentiate this from an inadvertent unsealing. This can preferably be brought about by the documentation device automatically changing the status of the container system 1 from "OK" to "blocked" when the unsealing is detected and logged (see table 1, row 5). An acoustic and/or optical signal requests the user to acknowledge the unsealing. If the acknowledgement by the user is forthcoming within a prescribed time, preferably within less than one minute or less than 30 seconds, in particular by means of a push-button 21, the acknowledgement is logged in the documentation device 5 and the status of the container system 1 is set to "OK" (see table 1, row 6).

The container system can now be filled at least in part with a medium by a user, with information relating to the filling time, the type and/or amount of the medium being stored in the documentation apparatus (see table 1, row 7). The temperature of the sample in the container 3 is measured continuously or periodically, in particular at intervals of approximately 10 s, by the temperature sensor 13, and the recorded measured value is stored in the storage apparatus 17 together with the recording time. The recorded measured values can be transmitted by a wireless connection by means of the RFID antenna to an external device for the purpose of further processing.

Figure 5:
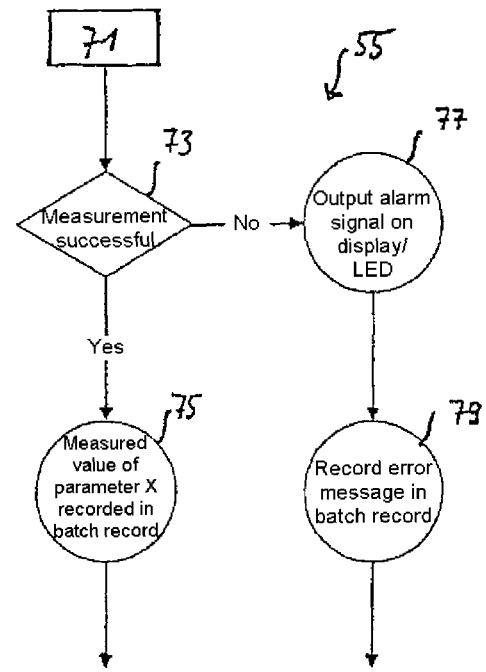
FIG. 5 shows a flowchart for recording a sensor measured value.

FIG. 5 shows the individual steps of the measured-value recording 55, which for example comprises the continuous or periodic measurement of the temperature by means of the temperature sensor 13 in a sensor-measured-value-recording step 71. A comparison step 73 establishes whether the sensor measured value was recorded successfully. By way of example, if the measured resistance of an NTC or PTC temperature sensor, or the temperature calculated therefrom, remains within prescribed limits, i.e. above and/or below specific (predetermined or predeterminable) values, the sensor device 13 outputs the corresponding measured value in an output step 75, which measured value is stored or documented by the documentation device 5. However, if the measurement is unsuccessful, e.g. because the temperature sensor is open or short-circuited, the sensor device 13 outputs an error message in an output step 77, which error message is logged or documented in step 79 by the documentation device together with the recording time.

After the container 3 has been emptied or the process has been completed by the user (see table 1, row 8), the container system 1 can, for example by actuating a switch 23, be blocked for further use (see table 1, row 9), i.e. the status of the container system is changed from "OK" to "B" for "blocked", particularly if the contents of the container system 1 are to be stored. The corresponding status change ("Container blocked on . . . ") is stored in the storage apparatus 17 together with the recording time. Inadvertent continued use can thus advantageously be prevented.

Should the contents of the container system 1 be used further, there may for example be a release for production purposes, which is logged or documented by the documentation device 5 (see table 1, row 10). If the container system 1, or the contents contained therein, reaches the use-by date or the expiry date stored in the documentation device 5, said documentation device 5 generates a system message that is logged, in particular automatically and/or without user intervention, wherein the status of the container system 1 is set to "blocked". An acoustic and/or visual indicator 27, 29 can indicate the blocking of the container system 1 (see table 1, row 11).

Before the container system 1 is permanently disposed of, the history of the container system stored in the storage apparatus 17 is read out, in particular in a wireless fashion by means of the RFID antenna, and is stored on an external data storage medium (see table 1, row 12).

TABLE 1

| No. | Time stamp | Action | Source | Status | Entry | Access |
|---|---|---|---|---|---|---|
| 1 | Mar. 4, 2008 10:25:30 | Initialization | Producer | B | Product data stored | Via receiving device |
| 2 | Mar. 4, 2008 15:10:12 | Release of the container system for delivery | Producer | OK | Release log stored | Via receiving device |
| 3 | Apr. 6, 2008 00:25:21 | Delivery | User Y | OK | Delivery reception stored | Via entry device |
| 4 | Apr. 6, 2008 09:20:30 | Release of the container system for use | User X | OK | Use-release stored | Via entry device |
| 5 | Apr. 7, 2008 06:10:45 | Unsealing | Product | B | Unsealing stored | Automatically generated system message, indicator |
| 6 | Apr. 7, 2008 06:11:00 | Unsealing confirmed | User Z | OK | Use-release stored | Via entry device |
| 7 | Apr. 7, 2008 07:15:25 | Filling | User Z | OK | Filling and type of contents stored | Via entry device |
| 8 | Apr. 8, 2008 09:10:23 | Completion of a manual operation | User Z | OK | Media and process information | Via entry device |

TABLE 1-continued

| No. | Time stamp | Action | Source | Status | Entry | Access |
|---|---|---|---|---|---|---|
| 9 | Apr. 8, 2008 12:10:04 | Transfer to storage | User Y | B | Transfer date and shelf life | Via entry device |
| 10 | May 12, 2008 15:10:01 | Release for production purposes | User Y | OK | Release reason and purpose stored | Via entry device, via receiving device |
| 11 | Jun. 8, 2008 12:10:04 | Reaching maximum storage time | Product | B | Use blocked because expiry date was reached | Automatically generated system message, indicator, message via transmitting device |
| 12 | Jun. 10, 2008 08:00:11 | Release for disposal | User W | OK | "Batch record" is archived | Via transmitting device |

The invention claimed is:

1. A container system (1), comprising:
a container (3) having an interior for containing a fluid and being sufficiently impermeable to prevent the fluid in the container from being displaced beyond geometric confines of the container (3), the container (3) having at least one connection (4a) for enabling selective filling of the fluid into the container (3) or selective emptying of the fluid from the container (3); and
an electronic documentation device (5) affixed to the container (3), wherein the documentation device (5) comprises:
at least one sensor device (13; 15) operative for measuring at least one value relating to the container or the fluid in the container,
at least one entry device (21; 23) that comprises at least one of a pushbutton (21), a switch (23) and a keyboard designed to record entries by manual actuation,
a timer (11) configured to identify a measurement occurrence time that exists for each measurement by the at least one sensor device (13; 15) and an entry recordal time that exists for each entry recorded by the at least one entry device (21; 23), and
a storage apparatus (17) associated with the at least one sensor device (13, 15), the at least one entry device (21; 23) and the timer (11), the storage apparatus (17) being configured to store each value measured by the at least one sensor device (13; 15) and the measurement occurrence time for the respective measured value and to store each entry recorded by the at least one entry device (21; 23) and the entry recordal time for each entry recorded by the at least one entry device (21; 23), such that the at least one stored value, the measurement occurrence time thereof, the at least one recorded entry and the entry recordal time thereof can be read.

2. The container system (1) of claim 1, wherein the container (3) consists of a flexible plastic.

3. The container system (1) of claim 2, wherein the container (3) is a disposable container (3).

4. The container system (1) of claim 1, further comprising at least one receiving device (25) designed to record a signal from an external device.

5. The container system (1) of claim 4, wherein the at least one receiving device (25) comprises at least one of an electromagnetic coupling element, a capacitive coupling element, an inductive coupling element and a direct coupling element.

6. The container system (1) of claim 1, wherein the container (3) has a sealing apparatus (9).

7. The container system (1) of claim 6, wherein the sealing apparatus (9) comprises at least one of a film, a metal conductor and an electrically conductive polymer.

8. The container system (1) of claim 6, wherein the at least one sensor device (15) detects the sealing state of the sealing apparatus (9), wherein the associated time of the recording corresponds to a break of the sealing apparatus (9).

9. The container system (1) of claim 1, wherein the at least one sensor device (13; 15) comprises at least one of a temperature sensor (13), a photosensor, an electrical resistance sensor (15), an electrical conductivity sensor and a pH sensor.

10. The container system (1) of claim 1, wherein the documentation device (5) furthermore comprises:
at least one indicator device (27; 29) for indicating a state of the documentation device (5) and/or contents stored in the storage apparatus (17) to a user.

11. The container system (1) of claim 10, wherein the at least one indicator device (27; 29) comprises at least one visual indicator (27) and/or at least one acoustic indicator (29) and/or at least one haptic indicator.

12. The container system (1) of claim 1, wherein the documentation device (5) furthermore comprises:
at least one transmitting device (31) to transmit a state of the documentation device (5) and/or contents stored in the storage apparatus (17) to an external device.

13. The container system (1) of claim 12, wherein the at least one transmitting device (31) comprises at least one of an electromagnetic coupling element and/or a capacitive coupling element and/or an inductive coupling element and/or a direct coupling element.

14. The container system (1) of preceding claim 1, wherein the documentation device (5) furthermore comprises a current source (33).

15. The container system (1) of claim 1, wherein the documentation device (5) furthermore comprises a signal-processing device (19).

16. The container system (1) of claim 1, wherein the documentation device (5) is flexible.

17. The container system (1) of claim 1, wherein the documentation device (5) is permanently connected to the container (3).

18. A method for using a container system (1), comprising the steps of:
providing a container (3) having an interior for containing a fluid and being sufficiently impermeable to prevent fluid in the container from being displaced beyond geometric confines of the container, the container having at least one connection (4a) for enabling selective filling of the fluid into the container (3) or selective emptying of the fluid from the container (3);

measuring at least one value relating to the container or the fluid in the container by using at least one sensor device (13; 15) on or in the container, identifying a measurement occurrence time that exists for each measurement by the at least one sensor device (13; 15), storing each value measured by the at least one sensor device (13; 15) and the measurement occurrence time for the respective measured value, recording the at least one value measured by the at least one sensor device by manually actuating at least one entry device (21; 23) that comprises at least one of a push-button (21), a switch (23) and a keyboard designed, identifying an entry recordal time that exists for each entry recorded by the at least one entry device (21; 23), storing each entry recorded by the at least one entry device (21; 23) and the entry recordal time for each entry recorded by the at least one entry device (21; 23), and transmitting to an external device each value measured by the at least one sensor device (13; 15), the measurement occurrence time for the respective measured value, each entry recorded by the at least one entry device (21; 23) and the entry recordal time for each entry recorded by the at least one entry device (21; 23).

19. The method of claim 18, furthermore comprising the step of:
attaching, at least in sections, the at least one sensor device (13, 15) onto the container (3).

20. The method of claim 18, furthermore comprising the step of:
synchronizing the timer (11).

21. The method of claim 18, furthermore comprising the step of:
closing the container (3) by means of a sealing apparatus (9).

22. The method of claim 18, furthermore comprising the step of:
sterilizing the container system (1).

23. The method of claim 18, furthermore comprising the step of:
storing the production date and/or the batch number and/or the expiry date in the storage apparatus (17).

\* \* \* \* \*